(12) United States Patent
Zhang et al.

(10) Patent No.: US 11,780,951 B2
(45) Date of Patent: Oct. 10, 2023

(54) CHAIN EXTENDER, PREPARATION METHOD AND APPLICATION THEREOF, RECYCLABLE THERMOSETTING POLYURETHANE AND PREPARATION METHOD THEREOF

(71) Applicant: Lanzhou Institute of Chemical Physics, Chinese Academy of Sciences, Lanzhou (CN)

(72) Inventors: Xinrui Zhang, Lanzhou (CN); Xiaoyue Wang, Lanzhou (CN); Zenghui Yang, Lanzhou (CN); Yaoming Zhang, Lanzhou (CN); Qihua Wang, Lanzhou (CN); Tingmei Wang, Lanzhou (CN)

(73) Assignee: Lanzhou Institute of Chemical Physics, Lanzhou (CN)

( * ) Notice: Subject to any disclaimer, the term of this patent is extended or adjusted under 35 U.S.C. 154(b) by 58 days.

(21) Appl. No.: 17/586,144

(22) Filed: Jan. 27, 2022

(65) Prior Publication Data

US 2022/0372206 A1    Nov. 24, 2022

(30) Foreign Application Priority Data

May 13, 2021    (CN) ............................ 202110521997

(51) Int. Cl.
  *C07C 319/22*    (2006.01)
  *C08G 18/38*    (2006.01)
  *C07C 323/37*    (2006.01)
  *C08G 18/10*    (2006.01)

(52) U.S. Cl.
  CPC ........ *C08G 18/3863* (2013.01); *C07C 319/22* (2013.01); *C07C 323/37* (2013.01); *C08G 18/10* (2013.01)

(58) Field of Classification Search
  CPC ........................... C07C 323/37; C07C 319/22
  See application file for complete search history.

(56) References Cited

FOREIGN PATENT DOCUMENTS

CN        110951023 B    *  1/2021

OTHER PUBLICATIONS

CN-110951023_B_01-2021_English.*

* cited by examiner

*Primary Examiner* — Michael L Leonard
(74) *Attorney, Agent, or Firm* — MILLEN, WHITE, ZELANO & BRANIGAN, P.C.; William Nixon (57) ABSTRACT

The present disclosure belongs to the technical field of polymer materials, and in particular relates to a chain extender and a preparation method and application thereof, a recyclable thermosetting polyurethane and a preparation method thereof. The present disclosure provides a chain extender whose chemical formula is shown in formula I. The chain extender provided by the present disclosure contains two types of dynamic covalent bonds, and the total number of dynamic covalent bonds is 4. The thermosetting polyurethane prepared by the provided chain extender has better hot-pressing repair efficiency. The results of the examples show that under the same hot-pressing conditions, the repair efficiency of the thermosetting polyurethane prepared by the 4,4'-dithiodianiline chain extender is 59%. The repair efficiency of thermosetting polyurethane is 97%, which is significantly improved.

11 Claims, 4 Drawing Sheets

CHAIN EXTENDER, PREPARATION METHOD AND APPLICATION THEREOF, RECYCLABLE THERMOSETTING POLYURETHANE AND PREPARATION METHOD THEREOF

CROSS REFERENCE TO RELATED APPLICATION

This patent application claims the benefit and priority of Chinese Patent Application No. 202110521997.5, filed on May 13, 2021, the disclosure of which is incorporated by reference herein in its entirety as part of the present application.

BACKGROUND

Field of the Invention

The present disclosure belongs to the technical field of polymer materials, in particular relates to a chain extender and a preparation method and application thereof, a recyclable thermosetting polyurethane and a preparation method thereof.

Description of the Related Technology

Polymer materials will inevitably appear micro-cracks or macro-cracks due to friction and wear, thermal fatigue, mechanical fatigue, etc. during use, which will affect the use of polymer materials.

In the prior art, in order to realize the recycling and reuse of thermosetting polyurethane through simple hot-pressing, a chain extender or crosslinking agent containing dynamic covalent bonds is generally introduced in the preparation process of polyurethane, and the dynamic covalent bonds at the fracture surface are used. Under the condition of hot-pressing, exchange and reconnect the polyurethane molecular chain to realize the purpose of recycling and reuse of polyurethane. Common dynamic covalent bonds include disulfide bond, imine bond, acylhydrazone bond, diselenide bond, Diels-Alder bond (DA bond) and so on.

However, polyurethane materials prepared by chain extenders or crosslinkers containing dynamic covalent bonds in the prior art have poor repair efficiency during hot-pressing.

SUMMARY

In view of this, the present disclosure provides a chain extender and a preparation method and application thereof, a recyclable thermosetting polyurethane and a preparation method thereof. The recyclable thermosetting polyurethane prepared by the chain extender provided by the present disclosure has higher heat pressure repair efficiency.

In order to achieve the above-mentioned purpose of the present disclosure, the present disclosure provides the following technical solutions:

The present disclosure provides a chain extender, a chemical formula is shown in formula I:

The present disclosure provides a method for preparing the chain extender described in the above technical solution, which comprises the following steps:

Mixing 4,4'-dithiodianiline, glutaraldehyde and polar organic solvents to perform aldimine condensation reaction to obtain the chain extender with the chemical formula shown in formula I;

The ratio of the amount of the glutaraldehyde terminal aldehyde functional group and the 4,4'-dithiodianiline terminal amino functional group is 1:(2-2.1).

Preferably, the polar organic solvent is an alcohol solvent.

Preferably, in the mixed solution obtained by mixing the 4,4'-dithiodianiline, glutaraldehyde and the polar organic solvent, the mass concentration of the 4,4'-dithiodianiline is 0.07-0.1 g/mL.

Preferably, the temperature of the aldimine condensation reaction is 15-30° C., and the time of the aldimine condensation reaction is 20-28 h.

Preferably, the system after the completion of the aldimine condensation reaction is purified, and the purified solvent is chloroform.

The present disclosure provides the application of the chain extender described in the above technical solution or the chain extender obtained by the preparation method described in the above technical solution in the preparation of thermosetting polyurethane.

The present disclosure provides a preparation method of recyclable thermosetting polyurethane, which comprises the following steps:

Mixing polyurethane prepolymer, chain extender and polar organic solvent for polymerization reaction to obtain elastomer solution;

Mixing the elastomer solution and the crosslinking agent and then curing to obtain the recyclable thermosetting polyurethane;

The chain extender is a chain extender obtained by the expansion connection described in the above technical solution or the preparation method described in the above technical solution.

Preferably, the ratio of the amount of the isocyanate functional group of the polyurethane prepolymer end group, the amino functional group of the chain extender end group and the hydroxyl functional group of the crosslinker end group is (2-2.2):(1-1.1):(1-1.1).

The present disclosure provides a recyclable thermosetting polyurethane prepared by the above preparation method.

The present disclosure provides a chain extender, the chemical formula is shown in formula I:

Formula I

Formula I

The chain extender provided by the present disclosure contains two disulfide bonds and two imine bonds. The chain extender provided by the present disclosure contains two types of multiple dynamic covalent bonds, and the total number of dynamic covalent bonds is 4. In addition, compared with the chain extender in the prior art, the thermosetting polyurethane prepared by the chain extender provided by the present disclosure has better hot-pressing repair efficiency. The results of the examples show that under the same hot-pressing conditions, the repair efficiency of the thermosetting polyurethane prepared by the 4,4'-dithiodianiline chain extender is 59%. The repair efficiency of thermosetting polyurethane is 97%, which is significantly improved.

The present disclosure provides the preparation method of the chain extender only using 4,4'-dithiodianiline and glutaraldehyde as raw materials, and by controlling the ratio of the molar amount of the terminal aldehyde functional group of glutaraldehyde and the 4,4'-dithiodianiline amino-terminal functional group are 1:(2-2.1), the chain extender can be prepared, and the process is simple and the preparation period is short.

DETAILED DESCRIPTION

The present disclosure provides a chain extender, the chemical formula is shown in formula I:

Mixing 4,4'-dithiodianiline, glutaraldehyde and polar organic solvents to perform aldimine condensation reaction to obtain the chain extender with the chemical formula shown in formula I;

The ratio of molar amount of the glutaraldehyde terminal aldehyde functional group and the 4,4'-dithiodianiline terminal amino functional group is 1:(2-2.1).

In the present disclosure, unless otherwise specified, the raw materials used are all commercially available products well known to those skilled in the art.

In the present disclosure, the 4,4'-dithiodianiline is preferably purchased from commercially available products. In a specific embodiment of the present disclosure, the 4,4'-dithiodianiline is purchased from Saan Chemical Technology (Shanghai) Co., Ltd.

In the present disclosure, the glutaraldehyde is preferably used in the form of a glutaraldehyde aqueous solution, and the mass percentage concentration of the glutaraldehyde aqueous solution is preferably 30-55%, more preferably 50%.

In the present disclosure, the polar organic solvent is preferably an alcohol solvent, more preferably methanol and/or ethanol.

In the present disclosure, in the mixed solution obtained by mixing the 4,4'-dithiodianiline, the aqueous glutaraldehyde solution and the polar organic solvent, the mass concentration of the 4,4'-dithiodianiline is preferably 0.07-0.1 g/mL, more preferably 0.08-0.09 g/mL; in the present disclosure, the color of the mixed solution obtained by mixing 4,4'-dithiodianiline, glutaraldehyde and polar organic solvent is brown.

In the present disclosure, the mixing preferably includes the following steps:

The 4,4'-dithiodianiline and part of the polar organic solvent are first mixed to obtain a 4,4'-dithiodianiline solution;

Performing a second mixing of the glutaraldehyde aqueous solution and the remaining polar organic solvent to obtain a glutaraldehyde mixed solution;

Formula I

The 4,4'-dithiodianiline solution and the glutaraldehyde mixed solution are subjected to a third mixing.

The chain extender provided by the present disclosure has two disulfide bonds and two imine bonds. When used as a chain extender of polyurethane, it can be prepared with a better hot-pressing repair efficiency.

The present disclosure provides a method for preparing the chain extender described in the above technical solution, which includes the following steps:

In the present disclosure, perform a first mixing of the 4,4'-dithiodianiline and part of the polar organic solvent to obtain a 4,4'-dithiodianiline solution; in the present disclosure, the mass percentage concentration of the 4,4'-dithiodianiline solution is 11-16%; in the present disclosure, the mixing is preferably carried out under stirring conditions, and the present disclosure has no special requirements for the specific implementation process of the stirring.

In the present disclosure, perform a second mixing of glutaraldehyde and the remaining polar organic solvent to obtain a glutaraldehyde mixed solution; in the present disclosure, the second mixing is preferably carried out under stirring conditions. There are no special requirements for the implementation process.

After obtaining the 4,4'-dithiodianiline solution and the glutaraldehyde mixed solution, the present disclosure performs the third mixing of the 4,4'-dithiodianiline solution and the glutaraldehyde mixed solution; in the present disclosure, the third mixing is preferably carried out under stirring conditions, and the present disclosure has no special requirements for the specific implementation process of the stirring.

In the present disclosure, the temperature of the aldimine condensation reaction is preferably 15-30° C., more preferably 18-25° C.; the time of the aldimine condensation reaction is preferably 20-28 h, more preferably 24 h.

In the present disclosure, it is preferable to determine the end point of the aldimine condensation reaction by the change of the color of the reaction system. When the color of the reaction system changes from the initial brown to light yellow and no longer changes, the present disclosure determines that the aldimine condensation reaction is complete.

In the present disclosure, it is preferable to purify the system after the aldimine condensation reaction is completed, and the purified solvent is preferably chloroform.

Before purification, the present disclosure preferably performs solid-liquid separation on the system after the aldimine condensation reaction is completed to obtain a solid product; in the present disclosure, the solid-liquid separation is preferably suction filtration. There are no special requirements for the specific implementation process.

After obtaining the solid product, the present disclosure preferably requires to purify the solid product; in the present disclosure, the purified solvent is preferably chloroform. In the present disclosure, the purification preferably includes mixing the solid product with chloroform and then leaving it to stand still. In the present disclosure, there is no special requirement on the amount of the chloroform, as long as the solid product can be completely impregnated. In the present disclosure, the standing time is preferably 3 to 5 h.

In the present disclosure, the purified solid product is preferably washed and dried; in the present disclosure, the washing is preferably ethanol washing. The present disclosure has no special requirements on the amount of ethanol. In the present disclosure, the number of times of washing is preferably 3 to 5 times; in the present disclosure, the chloroform is preferably removed by washing; in the present disclosure, the washed solid product is preferably dried. In the present disclosure, the drying temperature is preferably 50 to 60° C., so the drying time is based on drying the washed solid product to a constant weight.

In the present disclosure, 4,4'-dithiodianiline and glutaraldehyde are used as raw materials to prepare a chain extender with the structure shown in formula I through aldimine condensation reaction. The chain extender contains two disulfide bonds and two imine bonds; the color of the chain extender is yellow.

The present disclosure provides the application of the chain extender obtained by the chain extender described in the above technical solution or the preparation method described in the above technical solution in the preparation of polyurethane.

The chain extender provided by the present disclosure has the chemical formula shown in formula I and contains two disulfide bonds and two imine bonds. The thermosetting polyurethane prepared by the chain extender provided by the present disclosure has better repair efficiency.

The present disclosure provides a preparation method of recyclable thermosetting polyurethane, which comprises the following steps:

Mixing polyurethane prepolymer, chain extender and polar organic solvent for polymerization reaction to obtain elastomer solution;

Mixing the elastomer solution and the crosslinking agent and then curing to obtain the recyclable thermosetting polyurethane;

The chain extender is the chain extender described in the above technical solution or the chain extender obtained by the preparation method described in the above technical solution.

In the present disclosure, mixing a polyurethane prepolymer, a chain extender, and a polar organic solvent to carry out a polymerization reaction (hereinafter referred to as the first polymerization reaction) to obtain an elastomer solution.

The present disclosure has no special requirements on the source of the polyurethane prepolymer, and commercial products well-known to those skilled in the art can be used.

In the present disclosure, the preparation method of the polyurethane prepolymer preferably includes the following steps:

Mixing the polyester polyol and the isocyanate to perform a polymerization reaction (hereinafter referred to as a second polymerization reaction) to obtain the polyurethane prepolymer. In the present disclosure, the polyester polyol is preferably a polyester diol, more preferably a polycarbonate diol, and the relative molecular mass of the polycarbonate diol is preferably 2,000. The present disclosure has no special requirements on the source of the polyester polyol.

In the present disclosure, the isocyanate is preferably a diisocyanate, more preferably 4,4'-dicyclohexylmethane diisocyanate. The present disclosure has no special requirements on the source of the isocyanate.

In the present disclosure, the ratio of the molar amount of the hydroxyl functional group of the polyester polyol end group to the isocyanate functional group substance of the isocyanate end group is preferably 1:3.

In the present disclosure, the temperature of the second polymerization reaction is preferably 60-100° C., more preferably 80° C.; the time of the second polymerization reaction is preferably 1-5 h, more preferably 3 h.

In the present disclosure, the polar organic solvent is preferably N,N-dimethylformamide or dimethylsulfoxide, more preferably N,N-dimethylformamide.

In the present disclosure, the ratio of the amount of the isocyanate functional group of the end group of the polyurethane prepolymer and the amount of the amino functional group of the end group of the chain extender is preferably (2-2.2):(1-1.1), more preferably 2:1.

In the present disclosure, the mass ratio of the chain extender to the volume of the polar organic solvent is preferably (1-1.5) g:15 mL.

In the present disclosure, the temperature of the first polymerization reaction is preferably 60-100° C., more preferably 80° C.; the time of the second polymerization reaction is preferably 1-5 h, more preferably 3 h.

After obtaining the elastomer solution, mixing the elastomer solution of the present disclosure and the crosslinking agent and then curing to obtain the recyclable thermosetting polyurethane; the present disclosure has no special requirements on the type of crosslinking agent, the polyurethane crosslinking agent well known to those skilled in the art can be used; in specific embodiments of the present disclosure, the crosslinking agent is preferably an alcohol amine crosslinking agent, more preferably triethanolamine.

In the present disclosure, the ratio of molar amount of the isocyanate functional group of the end group of the polyurethane prepolymer and the hydroxyl functional group of the end group of the crosslinking agent is preferably (2-2.2): (1-1.1), more preferably 2:1.

The present disclosure has no special requirements on the specific implementation process of mixing the elastomer solution and the crosslinking agent.

In the present disclosure, the mixed solution obtained by mixing the elastic solution and the crosslinking agent is preferably dried. In the present disclosure, the drying is preferably vacuum drying, and the temperature of the vacuum drying is preferably 50-60° C. There is no special time requirement, as long as the solvent is completely removed.

In the present disclosure, the curing temperature is preferably 70-85° C., and the curing time is preferably 12-15 h.

The present disclosure provides a thermosetting polyurethane prepared by the above preparation method.

In the present disclosure, the polyurethane is preferably repaired under hot-pressing conditions. In a specific embodiment of the present disclosure, the hot-pressing temperature is preferably 60-80° C., more preferably 80° C.; The pressure is preferably 1 to 2 MPa; the hot-pressing time is preferably 10 to 12 h.

The thermosetting polyurethane provided by the present disclosure has better hot-pressing repair efficiency due to the structure of disulfide bond and imine bond.

The technical solutions of the present disclosure will be clearly and completely described below with reference to the embodiments of the present disclosure. Obviously, the described embodiments are only a part of the embodiments of the present disclosure, rather than all the embodiments. Based on the embodiments of the present disclosure, all other embodiments obtained by those of ordinary skill in the art without inventive work shall fall within the protection scope of the present disclosure.

Example 1

2.4837 g 4,4'-dithiodianiline and 20 mL ethanol were weighed in the reaction vessel, stirred and mixed until completely dissolved, and then 50% glutaraldehyde aqueous solution (1.0012 g) was added and dissolved in 5 mL ethanol under stirring conditions. After the addition was complete, the feeding port was closed, at this time the color of the mixed solution in the reactor was brown;

Then aldimine condensation reaction was carried out at 20° C. for 24 h, when the mixed solution in the reactor changed from brown to light yellow suspension, the raw material reaction was complete;

After the reaction, the reaction solution was left to stand and filtered with suction, washed with anhydrous ethanol three times and then dried at 50° C. to a constant weight to obtain a yellow powder, which was a chain extender product.

Figure 1:
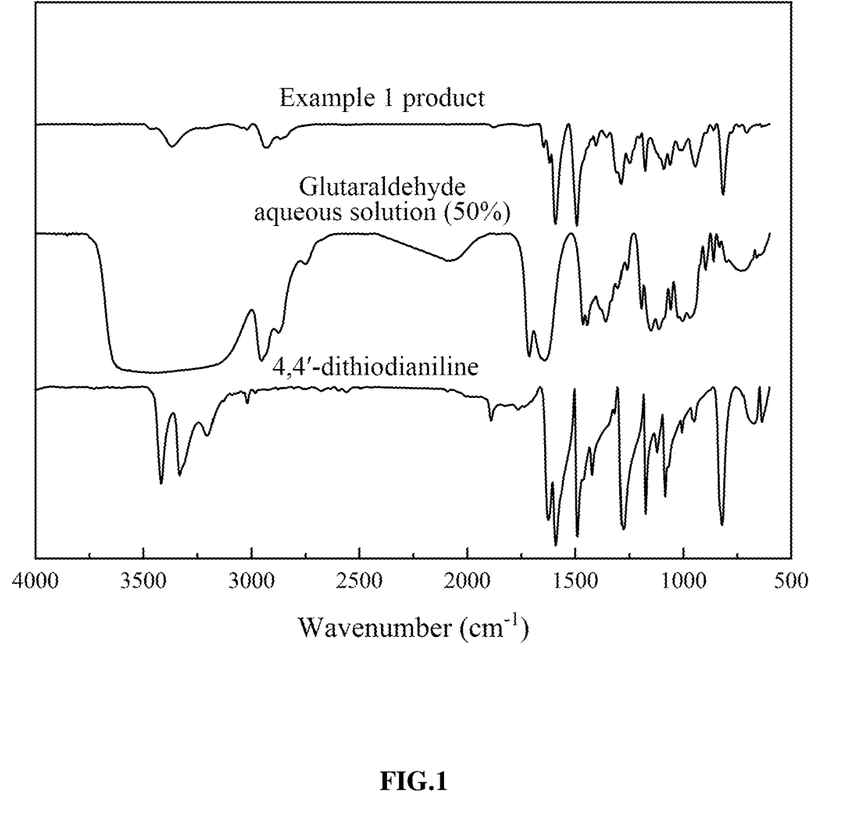
FIG. 1 is a Fourier Transform Infrared Spectroscopy of the chain extender prepared in Example 1 of the present disclosure.

The Fourier Transform Infrared Spectroscopy of the chain extender prepared in Example 1 is shown in FIG. 1. From FIG. 1, it can be observed that the amine group of 4,4'-dithiodianiline reacts with the aldehyde group of glutaraldehyde to form imine. In the figure, the characteristic peak at 1618 cm$^{-1}$ is the stretching vibration peak of the imine bond (—C=N—). The characteristic peaks at 2931 cm$^{-1}$ and 2864 cm$^{-1}$ are antisymmetric stretching vibration peak of methylene (—CH$_2$—) and symmetric stretching vibration peak, the characteristic peaks at 3467 cm$^{-1}$ and 3367 cm$^{-1}$ are the antisymmetric stretching vibration peak and symmetric stretching vibration peak of the primary amino group (—NH$_2$—), respectively. The above characteristic peaks can preliminarily prove the synthesis of the chain extender shown in formula I.

Figure 2:
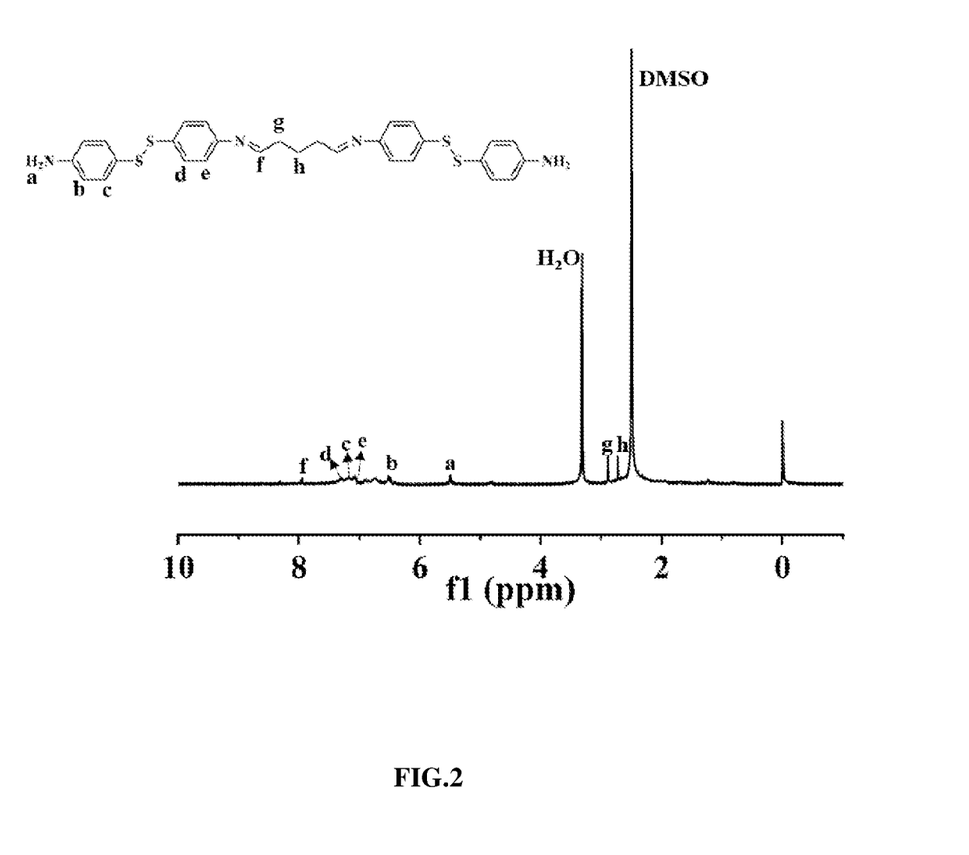
FIG. 2 is a Nuclear Magnetic Spectrogram of the chain extender prepared in Example 1 of the present disclosure.

The Nuclear Magnetic Resonance Spectra of the chain extender prepared in Example 1 is shown in FIG. 2. From FIG. 2, it can be drawn that the H chemical shift δ of each group of the chain extender synthesized in the present disclosure is: 1H NMR (400 MHz, DMSO) δ 7.95 (s, 1H), 7.29 (s, 2H), 7.18 (s, 2H), 7.07 (s, 2H), 6.52 (s, 2H), 5.49 (s, 2H), 2.89 (s, 2H), 2.73 (s, 2H). The NMR spectrum of FIG. 2 conforms to the chemical structure shown in Formula I.

Example 2

2.7321 g 4,4'-dithiodianiline and 30 mL ethanol were weighed in the reaction vessel, stirred and mixed until the dissolution is complete, then 50% glutaraldehyde aqueous solution (1.0012 g) was added and dissolved in 5 mL ethanol under stirring conditions. After the addition was complete, the feeding port was closed, at this time the color of the mixed solution in the reactor was brown;

Then aldimine condensation reaction was carried out at 20° C. for 24 h, when the mixed solution in the reactor changed from brown to light yellow suspension, the raw material reaction was complete;

After the completion of the reaction, the reaction solution was left to stand and filtered with suction, washed with absolute ethanol for 5 times, and then dried at 50° C. to a constant weight to obtain a yellow powder, which was a chain extender product.

The Fourier Transform Infrared Spectroscopy and Nuclear Magnetic Resonance Spectra of the product prepared in Example 2 were the same as those in Example 1.

Example 3

4.9674 g 4,4'-dithiodianiline and 40 mL ethanol were weighed in a reaction vessel, stirred and mixed until the dissolution was complete, then 50% glutaraldehyde aqueous solution (2.0024 g) was added and dissolved in 10 mL ethanol under stirring conditions. After the addition was complete, the feeding port was closed, at this time the color of the mixed solution in the reactor was brown;

Then aldimine condensation reaction was carried out at 20° C. for 24 h, when the mixed solution in the reactor changed from brown to light yellow suspension, the raw material reaction was complete;

After the reaction, the reaction solution was left to stand and filtered with suction, washed with absolute ethanol three times and then dried at 60° C. to a constant weight to obtain a yellow powder, which was a chain extender product.

The Fourier Transform Infrared Spectroscopy and Nuclear Magnetic Resonance Spectra of the product prepared in Example 3 were the same as those in Example 1.

Example 4

5.2157 g 4,4'-dithiodianiline and 50 mL ethanol were weighed in the reaction vessel, stirred and mixed until the dissolution was complete, then 50% glutaraldehyde aqueous solution (2.0024 g) was added and dissolved in 10 mL ethanol under stirring conditions. After the addition was complete, the feeding port was added, at this time the color of the mixed solution in the reactor was brown;

Then aldimine condensation reaction was carried out at 20° C. for 24 h, when the mixed solution in the reactor changed from brown to light yellow suspension, the raw material reaction was complete;

After the reaction, the reaction solution was left to stand and filtered with suction, washed 5 times with absolute ethanol, and dried at 55° C. to a constant weight to obtain a yellow powder, which was a chain extender product.

The Fourier Transform Infrared Spectroscopy and Nuclear Magnetic Resonance Spectra of the product prepared in Example 4 were the same as those in Example 1.

Example 5

5 g of polycarbonate diol (PCDL, $M_n \approx 2000$) and 2.045 mL of 4,4'-dicyclohexylmethane diisocyanate (HMDI) were added in a three-necked flask, and reacted at 80° C. for 3 h to obtain a polyurethane prepolymer. The chain extender prepared in Example 1 was dissolved in 15 mL of N,N-dimethylformamide and added to a three-necked flask to react for 3 h to complete the chain extension. Finally, the crosslinking agent triethanolamine (TEA) was added, and the organic solvent was removed in vacuum, cure at 80° C. for 12 h, finally a thermosetting polyurethane containing two disulfide bonds and two imine bonds is obtained.

Comparative Example 1

The preparation method was basically the same as that of Example 5, except that the chain extender is replaced with 4,4'-dithiodianiline to obtain a thermosetting polyurethane containing only disulfide bond.

Test Example 1

Figure 4:
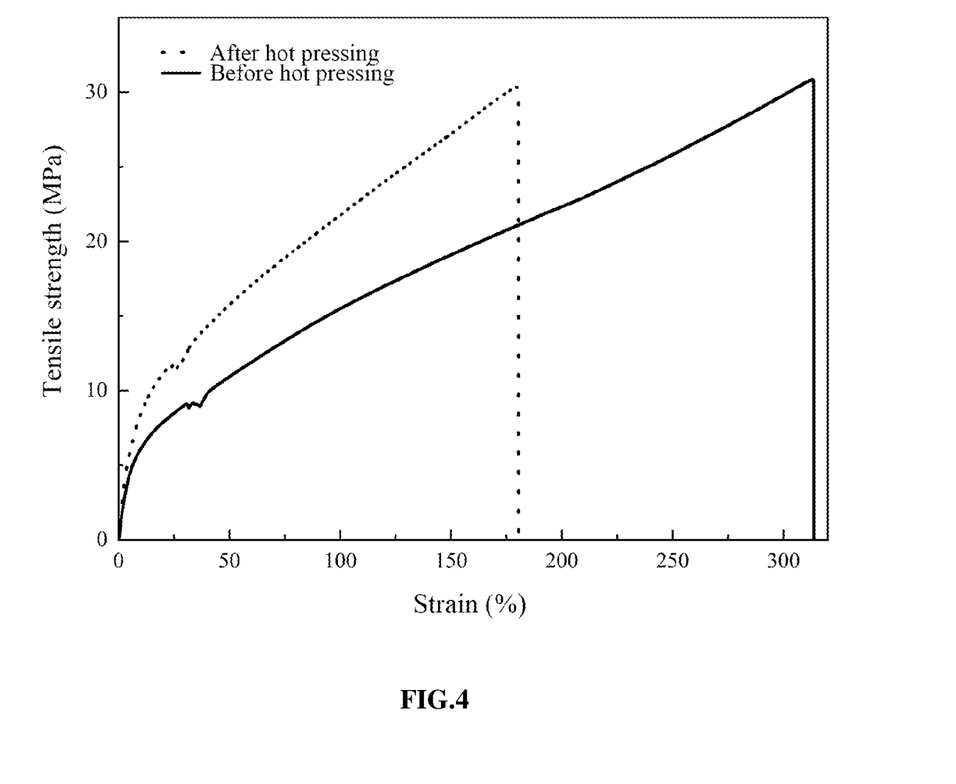
FIG. 4 is the tensile test results of the thermosetting polyurethane product prepared in Example 5 of the present disclosure before and after hot-pressing.

According to GB/T 528-2009, the polyurethane prepared in Example 5 and Comparative Example 1 was subjected to tensile test; then, the two polyurethanes obtained in Example 5 and Comparative Example 1 were cut into pieces, and the size of the obtained polyurethane fragments was within two millimeters, the two polyurethane scraps are then hot-pressed at 80° C. under a pressure of 2 MPa for 12 h to complete the hot-pressing repair of the scraps, and the repaired polyurethane is obtained; the polyurethane obtained after the hot-pressing of the scraps was subjected to a tensile test, FIG. 4 is a comparison diagram of tensile test results of the product prepared in Example 5 and the product of crushed material hot-pressed.

According to $$\eta(\%) = \frac{\sigma_h}{\sigma_0} \times 100\%,$$

$\sigma_0$ is the tensile strength of the original material, and $\sigma_h$ is the tensile strength after hot-pressing. Calculate the hot-pressing repair efficiency of the polyurethane, which is calculated from FIG. 4, the efficiency of hot-pressing repair of thermosetting polyurethane containing two disulfide bonds and two imine bonds prepared in Example 5 of the present disclosure reached 97%.

Figure 3:
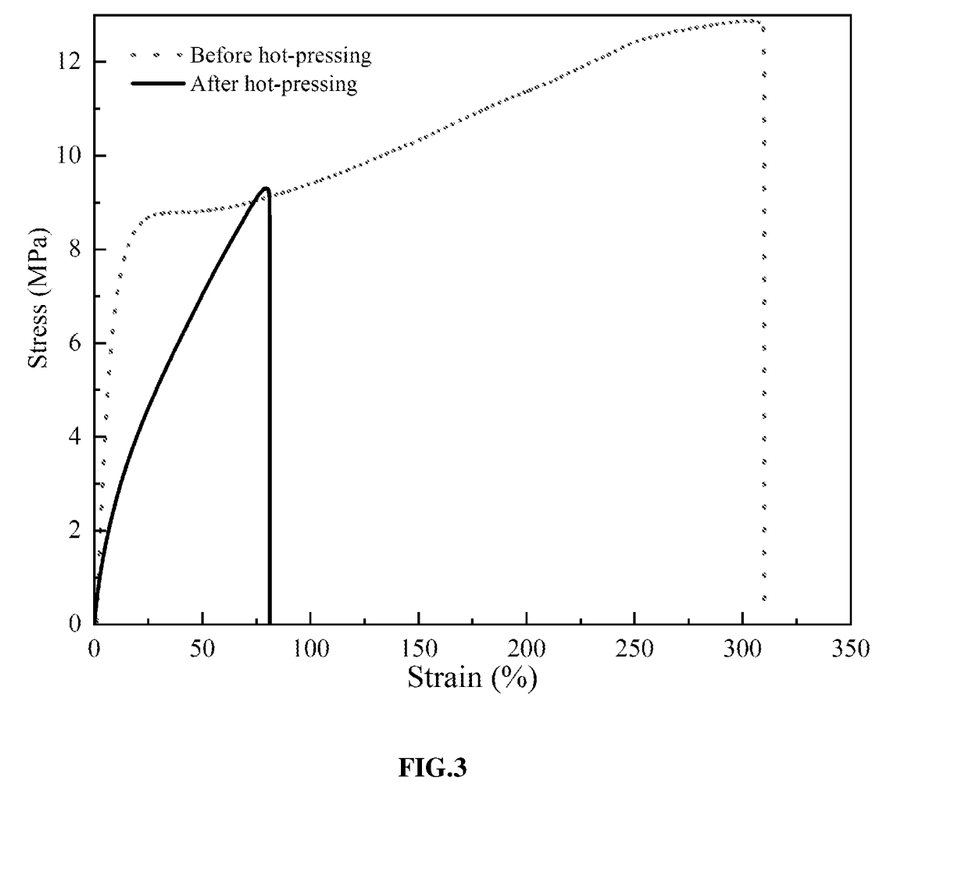
FIG. 3 is the tensile test results of the thermosetting polyurethane product prepared in Comparative Example 1 of the present disclosure before and after hot-pressing.

FIG. 3 is a comparison diagram of the tensile test results of the product prepared in Comparative Example 1 and the product of scrap; calculated from FIG. 3, the thermosetting polyurethane prepared in Comparative Example 1 of the present disclosure contains a thermosetting polyurethane containing only disulfide bond. The repair efficiency is 59%.

The above test results fully prove that the chain extender prepared by the present disclosure can provide better hot-pressing repair efficiency for polyurethane materials than the general chain extender (4,4'-dithiodianiline).

Moreover, since the polyurethane prepared by the present disclosure has a high-efficiency hot-pressing repair capability, the service life of the polyurethane is also improved.

The above are merely the preferred embodiments of the present disclosure. It should be noted that for those of ordinary skill in the art, improvements and modifications can be made without departing from the principle of the present disclosure, and these improvements and modifications are should also be regarded as the protection scope of the present disclosure.

What is claimed is:

1. A chain extender, wherein the chemical formula is as shown in formula I:

Formula I

2. A preparation method for the chain extender according to claim 1, wherein it comprises the following steps:
   mixing 4,4'-dithiodianiline, glutaraldehyde and polar organic solvents to perform aldimine condensation reaction to obtain the chain extender with the chemical formula shown in formula I; wherein a ratio of molar amount of the glutaraldehyde terminal aldehyde functional group and the 4,4'-dithiodianiline terminal amino functional group is 1: (2-2.1).

3. The preparation method according to claim 2, wherein the polar organic solvent is an alcohol solvent.

4. The preparation method according to claim 2, wherein, in the mixed solution obtained by mixing 4,4'-dithiodianiline, glutaraldehyde and polar organic solvent, the mass concentration of 4,4'-dithiodianiline is 0.07-0.1 g/mL.

5. The preparation method according to claim 3, wherein, in the mixed solution obtained by mixing 4,4'-dithiodianiline, glutaraldehyde and polar organic solvent, the mass concentration of 4,4'-dithiodianiline is 0.07-0.1 g/mL.

6. The preparation method according to claim 2, wherein a temperature of the aldimine condensation reaction is 15-30° C., and a time of the aldimine condensation reaction is 20-28 h.

7. The preparation method according to claim 2, wherein, after the aldimine condensation reaction, the preparation method further comprises: purifying the obtained reaction product, and a purified solvent is chloroform.

8. A preparation method for preparing recyclable thermosetting polyurethane, comprising the following steps:

mixing polyurethane prepolymer, chain extender and polar organic solvent for polymerization reaction to obtain an elastomer solution;

mixing the elastomer solution and the crosslinking agent and then curing to obtain the recyclable thermosetting polyurethane; wherein the chain extender is the chain extender according to claim 1.

9. The preparation method according to claim 8, wherein a ratio of molar amount of an isocyanate functional group of the polyurethane prepolymer end group, an amino functional group of the chain extender and a hydroxyl functional group of the crosslinker is (2-2.2):(1-1.1):(1-1.1).

10. The recyclable thermosetting polyurethane prepared by the preparation method of claim 8.

11. The recyclable thermosetting polyurethane prepared by the preparation method of claim 9.

\* \* \* \* \*